(12) United States Patent
Katzir et al.

(10) Patent No.: US 9,133,506 B2
(45) Date of Patent: Sep. 15, 2015

(54) METHODS AND SYSTEMS FOR ANALYZING BIOLOGICAL SAMPLES

(75) Inventors: Nir Katzir, Givat Elah (IL); Tsafrir Kolatt, Haifa (IL); Irit Bar-Am, Herzlia (IL)

(73) Assignee: Applied Spectral Imaging Ltd., Yokneam (IL)

( * ) Notice: Subject to any disclaimer, the term of this patent is extended or adjusted under 35 U.S.C. 154(b) by 1442 days.

(21) Appl. No.: 12/087,543

(22) PCT Filed: Jan. 9, 2007

(86) PCT No.: PCT/IL2007/000034
§ 371 (c)(1),
(2), (4) Date: Jul. 9, 2008

(87) PCT Pub. No.: WO2007/080583
PCT Pub. Date: Jul. 19, 2007

(65) Prior Publication Data
US 2009/0048785 A1 Feb. 19, 2009

Related U.S. Application Data

(60) Provisional application No. 60/757,464, filed on Jan. 10, 2006.

(51) Int. Cl.
*G06F 19/20* (2011.01)
*C12Q 1/06* (2006.01)
*C12Q 1/68* (2006.01)
*G06K 9/00* (2006.01)

(52) U.S. Cl.
CPC .......... *C12Q 1/6841* (2013.01); *G06K 9/00134* (2013.01)

(58) Field of Classification Search
None
See application file for complete search history.

(56) References Cited

U.S. PATENT DOCUMENTS

| 5,254,845 | A | 10/1993 | Burgess et al. |
|---|---|---|---|
| 6,169,816 | B1 | 1/2001 | Ravkin |
| 6,215,892 | B1 | 4/2001 | Douglass et al. |
| 6,259,807 | B1 | 7/2001 | Ravkin |
| 6,418,236 | B1 | 7/2002 | Ellis et al. |
| 6,633,662 | B2 | 10/2003 | Ravkin |
| 6,718,053 | B1 | 4/2004 | Ellis et al. |
| 6,900,426 | B2 | 5/2005 | Zhang |
| 2004/0137470 | A1* | 7/2004 | Dhallan ............................ 435/6 |
| 2004/0197839 | A1 | 10/2004 | Daniely et al. |
| 2005/0250111 | A1 | 11/2005 | Xie et al. |
| 2005/0265588 | A1* | 12/2005 | Gholap et al. ................ 382/128 |
| 2009/0253145 | A1* | 10/2009 | Kilpatrick et al. ................ 435/6 |

FOREIGN PATENT DOCUMENTS

| WO | WO 02/47392 | 6/2002 |
|---|---|---|
| WO | WO 03/014795 | 2/2003 |
| WO | WO 03/060653 | 7/2003 |
| WO | WO 2007/080583 | 7/2007 |

OTHER PUBLICATIONS

International Search Report Dated Oct. 1, 2008 From the International Searching Authority Re.: Application No. PCT/IL07/00034.
Written Opinion Dated Oct. 1, 2008 From the International Searching Authority Re.: Application No. PCT/IL07/00034.
Netten et al. "FISH and Chips: Automation of Fluorescent Dot Counting in Intel-phase Cell Nuclei", Cytometry, 28: 1-10, 1997.
Plesch et al. "Metafer—A Novel Ultra High Throughput Scanning System for Rarc Cell Detection and Automatic Interpahse FISH Scoring", In: 'Early Prenatal Diagnosis, Fetal Cells and DNA in the Mother, Present State and Perspectives', 12th Fetal Cell Workshop, Prague, p. 329-339, 2001.
International Preliminary Report on Patentability Dated Jan. 22, 2009 From the International Bureau of WIPO Re.: Application No. PCT/IL2007/000034.

* cited by examiner

*Primary Examiner* — John S Brusca

(57) ABSTRACT

Methods, computer readable storage media and systems which can be used for analyzing labeled biological samples, identifying chromosomal aberrations, identifying genetically abnormal cells and/or computationally scanning the samples using randomly or randomized scanning methods are provided. Specifically, the present invention can be used to analyze FISH-stained samples and automatically identify chromosomal aberrations associated with abnormal intensity ratio of stained occurrences in the sample.

21 Claims, 5 Drawing Sheets
(3 of 5 Drawing Sheet(s) Filed in Color)

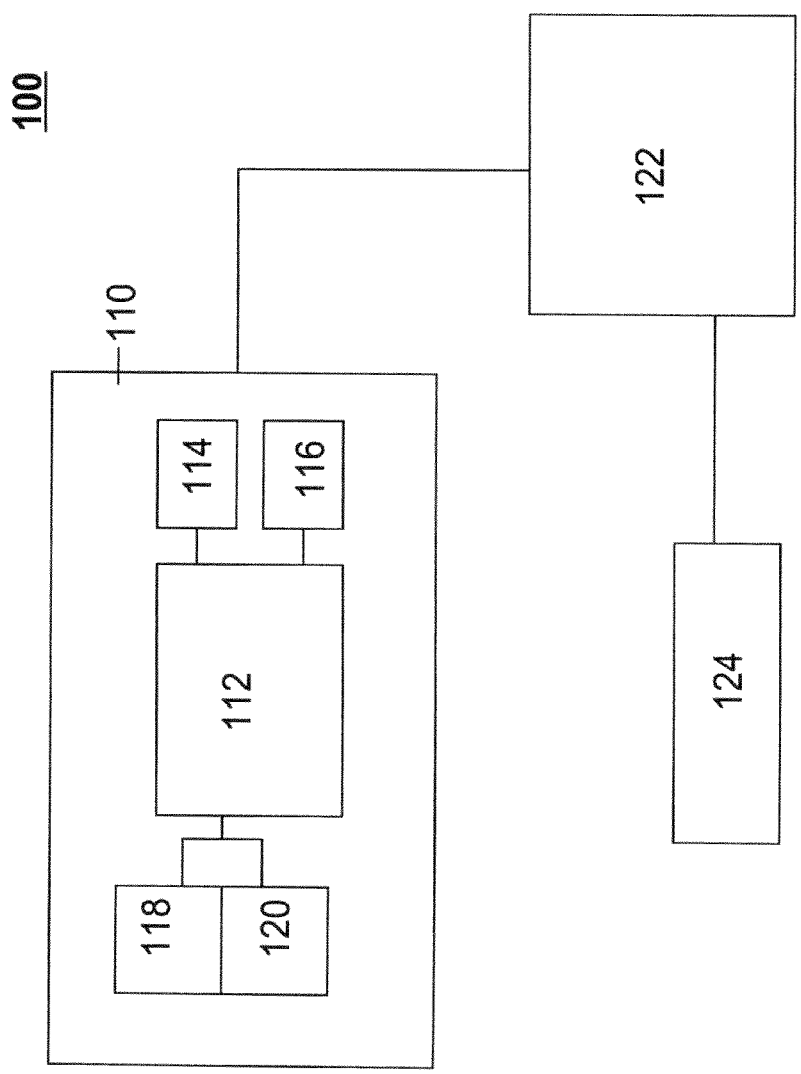

METHODS AND SYSTEMS FOR ANALYZING BIOLOGICAL SAMPLES

RELATED APPLICATIONS

This Application is a National Phase of PCT Patent Application No. PCT/IL2007/000034 having International Filing Date of Jan. 9, 2007, which claims the benefit of U.S. Provisional Patent Application No. 60/757,464 filed on Jan. 10, 2006. The contents of the above Applications are all incorporated herein by reference.

FIELD AND BACKGROUND OF THE INVENTION

The present invention relates to methods, computer readable storage media and systems for analyzing labeled biological samples such as fluorescence in situ hybridization (FISH)—stained samples, such as for identifying chromosomal aberrations, for identifying genetically abnormal cells and for computational scanning of samples.

Various pathologies such as infections, inflammation, cancer and/or genetic diseases are currently diagnosed by analyzing microscopic slides containing biological specimens such as blood samples, urine sample, tissue biopsies, spinal fluid aspirates, amniotic fluid, chorionic villi sample (CVS) and the like. Since most of the biological samples are transparent, the first step of analysis requires staining with a specific dye or probe which enables the detection of almost any tissue or cellular specimen constituent. Such constituents may be, for example, a connective tissue, a cell organelle (e.g. mitochondria), a certain protein or DNA sequence, a specific chromosomal region and/or a specific RNA transcript. Common staining methods include cytological staining (e.g., Giemsa, Hematoxylin), immunological staining (e.g., immunohistochemistry, immunofluorescence), activity staining (e.g., using fluorescent or chromogenic substrates), cytogenetic staining (e.g., G-banding or R-banding), in situ chromosomal staining (e.g., using FISH) and/or in situ DNA staining [e.g., using quantitative-FISH (Q-FISH)]. The dyes or probes used in such staining methods can be detected using bright-field microscopy with transmitted light, fluorescence microscopy or both. Most of the staining methods utilize commercial kits with all necessary chemicals and stains for labeling and detection. Once the sample is stained, it can be viewed using a microscope or an imaging system either manually by eye observation or automatically using a computer-controlled analysis system. Most imaging systems are based on charged coupled device (CCD) camera detectors that are controlled by a computer and appropriate acquisition control and image analysis software. Other imaging systems use a point detector such as photomultiplier (PMT) and a focused laser source and scan the image point-by-point.

The first step in applying these imaging systems involves the identification of regions of interests (ROIs) on the microscopic slide. In many research and clinical applications, the user manually scans the microscopic slide and then captures the ROIs for further analysis. However, since manual identification of ROIs is a time- and labor-consuming effort, which complicates the overall analysis process, systems for automatically scanning and analyzing biological samples have been developed. Such systems usually combine a microscope setup, an imaging device such as a CCD camera together with a computer-controlled hardware that allows scanning of the sample in three dimensions (3D) with high accuracy and precision [see for example, H. Netten et al., 1997, Cytometry 28: 1-10 or the CytoVision SPOT system by Applied Imaging Corporation, San Jose Calif., USA)]. A typical automated system includes optical elements (e.g., a color filter), a control over stage movement, which enables the scanning of all desired areas, and a correlation of stage motion with image detection (using e.g., the CCD detector). Such an automated system also requires the ascertainment of the correct focus (i.e., the z-position) of the sample so that the detected object is in the correct focal plane of the microscope and the selection of the optimal exposure time of the camera and of other acquisition parameters.

Because of the large area that has to be scanned on the microscope slide and the typically high resolution that is needed, many images have to be scanned from each slide. This requires a certain strategy for scanning the relevant slide-area in an efficient way. Currently practiced methods of scanning the ROIs begin with the center of slide and proceed in a circular manner outward, moving from one ROI to an adjacent one. However, if the cells to be scanned are not evenly distributed on the slide, scanning may begin with an area that is completely irrelevant for analysis, thus resulting in a considerable waist of scanning time until reaching the areas containing cells. In addition, in many cases, the cells of interest (e.g., cancerous cells), which are part of a tissue sample, are not positioned in the center of the specimen, thus leading to either mis-diagnosis due to under-scanned areas or to enormously long scanning times which are impractical for both research and clinical applications. To date, there is no available method which can efficiently select ROIs in a reliable and time-consuming manner.

The detection of multiple fluorescent probes and automation of analysis is of significant advantage in the application of fluorescence in situ hybridization (FISH). FISH is employed to map the precise location of genes on chromosomes, and to detect very small genetic defects not visible by gross staining of chromosomes (e.g., by G-banding or R-banding). Thus, FISH staining is widely used for detection of genetic aberrations at the chromosome level (e.g., chromosome amplification, deletion, translocation, rearrangement) [H. Netten et al., FISH and Chips: Automation of Fluorescent Dot Counting in Interphase Cell Nuclei. Cytometry 28: 1-10 (1997)]. Many FISH applications merely require the cytogeneticist to look through the eyepieces of a microscope, or at the image on the monitor, and to determine whether a fluorescent label is present or absent. With somewhat more complex specimens, a simple count of one or two colored labels may be done (e.g., for determination of gender using probes from the X and Y chromosomes). Other applications require the enumeration of different fluorescent signals in each cell and the determination of a ratio therebetween. For example, the amplification of the Her-2 gene, which is used in staging and/or determining the prognosis of stage II, node-positive, breast cancer patients, can be detected using the PathVision kit (Vysis Inc. Chicago Ill., USA). Such a kit includes a FISH probe for the Her-2 gene (labeled with a SpectrumOrange™ fluorochrome) and a FISH probe for the centromere of chromosome 17 (SpectrumGreen™). Other FISH probes can be used to detect various translocations by detecting merged fluorescent signals. For example, the BCR/abl ES kit (e.g. Vysis Inc. Chicago Ill., USA) can be used to diagnose the presence of a Philadelphia chromosome, which is associated with chronic myeloid leukemia (CML), by detecting the presence of merged fluorescent signals resulting from fusion of chromosomes 9 and 22. Although chromosomal translocations may also result in reduced intensity of staining of one stained spot as compared to another spot labeled with the same probe, as was unintentionally shown in the case of the unbalanced translocation involving chromosomes 18 and 20

[t(18;20)(p11.1;p11.1)] (Czako M., et al., 2002 (Am. J. Med. Genet. 108: 226-8)), currently practiced FISH analysis methods do not include and/or rely on the relative intensity measurements of the same probe as part of a routine FISH analysis.

For most clinical and research applications, the FISH results are being interpreted automatically using image analysis systems. One of the main problems associated with the currently available automated image analysis techniques is the presence of split, merged or overlapping spots resulting from either technical reasons or associated with the presence of translocations and/or sub-deletions which are difficult to interpret. For example, a merged spot of two different probes (labeled with different fluorescent dyes) can result from either a real translocation of the two separate chromosome sequences, or from an accidental close proximity of these two chromosome sequences (that is known to happen occasionally). In addition, a single spot on a single chromosome locus can appear as a split-spot with two close-by spots if the observed chromosome contains already two copies of the genome (after the S-phase of the cell cycle) and the two chromatids of the chromosome are somewhat far apart. In addition, stain debris may show up as extra spots which can mistakenly be counted as additional "real" spots. Moreover, the hybridization conditions may be sub-optimal, thus resulting in non-specific binding of probe and extra background stain which may lead to false analysis of the image.

Existing imaging systems currently include either a monochrome camera or a color camera for image analysis. While bright field and simple FISH probes with only 1-3 colors can be imaged and analyzed in a single exposure using a color camera, most of FISH and especially multi-color FISH probes need to be imaged with multiple acquisitions through different excitation and emission color filters using a monochrome camera. A color camera has three color filters that would usually not match the emission spectral ranges of the fluorochromes, and therefore a monochrome camera is much more favorable. Thus, if the imaging system includes only a color camera, it can result in poor quality and signal to noise measurements of the weak fluorescent staining. On the other hand, if the imaging system includes a monochrome camera, measurements of the bright signals, which are often performed using a bright field mode, but sometimes also using a fluorescent mode, are time-consuming and complicated.

There is thus a widely recognized need for, and it would be highly advantageous to have, image analysis methods and systems devoid of the above limitations.

SUMMARY OF THE INVENTION

According to one aspect of the present invention there is provided a method of analyzing a labeled biological sample, the method comprising measuring a relative amount of at least one label having at least two occurrences in the labeled biological sample, thereby analyzing the labeled biological sample.

According to another aspect of the present invention there is provided a method of identifying a chromosomal aberration comprising measuring a relative amount and optionally a frequency of at least one label of a nucleic acid probe, the at least one label having at least two occurrences in a sample, wherein the relative amount and optionally the frequency of the at least one label in the sample are indicative of the chromosomal aberration, thereby identifying the chromosomal aberration.

According to yet another aspect of the present invention there is provided a method of identifying a genetically abnormal cell in a sample, the method comprising measuring in a cell a relative amount and optionally a frequency of at least one label of a nucleic acid probe, the at least one label having at least two occurrences in the sample, wherein the relative amount and optionally the frequency of the at least one label in the cell are indicative of a chromosomal aberration, thereby identifying the genetically abnormal cell in the sample.

According to still another aspect of the present invention there is provided a computer readable storage medium comprising a set of instructions for analyzing a labeled biological sample, the set of instructions comprises a routine for measuring a relative amount of at least one label having at least two occurrences in the labeled biological sample, thereby analyzing the labeled biological sample.

According to an additional aspect of the present invention there is provided a computer readable storage medium comprising a set of instructions for identifying a chromosomal aberration, the set of instructions comprises a routine for measuring a relative amount and optionally a frequency of at least one label of a nucleic acid probe, the at least one label having at least two occurrences in a sample, wherein the relative amount and optionally the frequency of the at least one nucleic acid probe in the sample are indicative of the chromosomal aberration, thereby identifying the chromosomal aberration.

According to yet an additional aspect of the present invention there is provided a computer readable storage medium comprising a set of instructions for identifying a genetically abnormal cell in a sample, the set of instructions comprises a routine for measuring in a cell a relative amount and optionally a frequency of at least one label of a nucleic acid probe, the at least one label having at least two occurrences in the sample, wherein the relative amount and optionally the frequency of the at least one label in the cell are indicative of the chromosomal aberration, thereby identifying the genetically abnormal cell in the sample.

According to still an additional aspect of the present invention there is provided a method of scanning a sample, the method comprising sequentially scanning areas being farthest from previously scanned areas in the sample, thereby scanning the sample.

According to a further aspect of the present invention there is provided a computer readable storage medium comprising a set of instructions for scanning a sample, the set of instructions comprises a routine for sequentially scanning areas being farthest from previously scanned areas in the sample, thereby scanning the sample.

According to yet a further aspect of the present invention there is provided a method of scanning a sample, the method comprising randomly scanning an area of at least a portion of a plurality of selected sub-regions of the sample, thereby scanning the sample.

According to still a further aspect of the present invention there is provided a computer readable storage medium comprising a set of instructions for scanning a sample, the set of instructions comprises a routine for randomly scanning an area of at least a portion of a plurality of selected sub-regions of the sample, thereby scanning the sample.

According to still a further aspect of the present invention there is provided a system for analyzing a labeled biological sample comprising: (i) an input unit for receiving data of the labeled biological sample; and (ii) an analyzer associated with the input unit, the analyzer being for measuring a relative amount of at least one label having at least two occurrences in the labeled biological sample.

According to still a further aspect of the present invention there is provided a system for identifying a chromosomal aberration in a labeled sample comprising: (i) an input unit for receiving data of the labeled sample; and (ii) an analyzer associated with the input unit, the analyzer being for measuring a relative amount and optionally a frequency of at least one label of a nucleic acid probe, the at least one label having at least two occurrences in the sample, wherein the relative amount and optionally the frequency of the at least one nucleic acid probe in the sample are indicative of the chromosomal aberration.

According to still a further aspect of the present invention there is provided a system for identifying a genetically abnormal cell in a labeled sample comprising: (i) an input unit for receiving data of the labeled sample; and (ii) an analyzer associated with the input unit, the analyzer being for measuring in a cell a relative amount and optionally a frequency of at least one label of a nucleic acid probe, the at least one label having at least two occurrences in the sample, wherein the relative amount and optionally the frequency of the at least label in the sample are indicative of a chromosomal aberration and the genetically abnormal cell.

According to further features in preferred embodiments of the invention described below, the relative amount comprises computationally scanning the sample.

According to still further features in the described preferred embodiments the scanning comprises randomly scanning the sample.

According to still further features in the described preferred embodiments the scanning comprises randomized scanning of the sample.

According to still further features in the described preferred embodiments the randomized scanning comprises randomly scanning an area of at least a portion of a plurality of selected sub-regions of the sample.

According to still further features in the described preferred embodiments the randomized scanning comprises sequentially scanning areas being farthest of pre-scanned areas in the sample.

According to still further features in the described preferred embodiments the scanning comprises computationally scanning the sample.

According to still further features in the described preferred embodiments the computationally scanning is effected by a computer-controlled imaging system.

According to still further features in the described preferred embodiments the computer-controlled imaging system comprises an optical microscope, a digital imaging system and a computer.

According to still further features in the described preferred embodiments the digital imaging system comprises at least one camera selected from the group consisting of a monochrome camera and a color camera.

According to still further features in the described preferred embodiments the digital imaging system comprises a monochrome camera and a color camera.

According to still further features in the described preferred embodiments the computer readable storage medium further comprising an algorithm for selecting one of the monochrome camera and the color camera.

According to still further features in the described preferred embodiments the at least two occurrences are comprised in a single cell.

According to still further features in the described preferred embodiments the at least two occurrence are comprised in different cells.

According to still further features in the described preferred embodiments the chromosomal aberration is selected from the group consisting of a deletion, a translocation, a gain of chromosome or a portion thereof, a loss of chromosome or a portion thereof, an inversion, a balanced translocation and an imbalanced translocation.

According to still further features in the described preferred embodiments the chromosomal aberration is associated with a chromosomal locus selected from the group consisting of BCR/ABL, Tel/AML, PML/RARA, CBFB, MLL, BCL6, MYC, IGH, ALK, IGH/BCL2, IGH/MYC and AML/ETO.

According to still further features in the described preferred embodiments the sample comprises a DNA sample or an RNA sample.

According to still further features in the described preferred embodiments the sample comprises labeled biomolecules selected from the group consisting of lipids, polypeptides, polynucleotides and carbohydrate.

According to still further features in the described preferred embodiments the sample comprises a tissue biopsy, a CSF sample, a urine sample, a blood sample, a bone marrow sample, a fetal sample and/or a skin sample.

According to still further features in the described preferred embodiments the input unit comprises a computer-controlled imaging system.

According to still further features in the described preferred embodiments the monochrome camera comprises a black and white array detector.

According to still further features in the described preferred embodiments the color camera allows measuring of at least two color channels.

According to still further features in the described preferred embodiments the color camera allows measuring of at least three color channels.

According to still further features in the described preferred embodiments the method further comprising correlating the relative amount to an amount index following measuring the relative amount.

According to still further features in the described preferred embodiments the method further comprising correlating the frequency of the at least one label to a frequency index following measuring the frequency of at least one label.

According to still further features in the described preferred embodiments the at least two occurrences are comprised in a single cell of the sample.

According to still further features in the described preferred embodiments the at least one nucleic acid probe is a FISH probe.

According to still a further aspect of the present invention there is provided a method of analyzing a labeled biological sample, the method comprising:
 (a) sorting at least one non-classified object of the biological sample according to a difference from a classified object-of-interest; and
 (b) signaling a signal to alert a detection of the difference; thereby analyzing the labeled biological sample.

According to still a further aspect of the present invention there is provided a computer readable storage medium comprising a set of instructions for analyzing a labeled biological sample, the set of instructions comprises a routine for (a) sorting at least one non-classified object of the biological sample according to a difference from a classified object-of-interest; and (b) signaling a signal to alert a detection of the difference, thereby analyzing the labeled biological sample.

According to still a further aspect of the present invention there is provided a system for analyzing a labeled biological sample comprising:
 (i) an input unit for receiving data of the labeled biological sample; and (ii) an analyzer associated with the input unit, the analyzer being for sorting at least one non-classified object of the biological sample according to a difference from a classified object-of-interest, and signaling a signal to alert a detection of the difference.

According to still further features in the described preferred embodiments the at least one non-classified object comprises a plurality of non-classified objects and whereas the difference is a minimal difference from the classified object-of-interest.

According to still further features in the described preferred embodiments the difference comprises a difference in a number of occurrences of at least one label of the labeled biological sample.

According to still further features in the described preferred embodiments the difference comprises a difference in a relative amount of the at least one label of the biological sample.

According to still further features in the described preferred embodiments the sorting further comprises generating a similarity index, wherein a plurality of distinguishable signals is assigned to a plurality of differences, whereby the signal corresponds to the difference.

According to still further features in the described preferred embodiments the object comprises a cell.

According to still further features in the described preferred embodiments the object comprises a cell component.

According to still further features in the described preferred embodiments the labeled biological sample is FISH labeled.

The present invention successfully addresses the shortcomings of the presently known configurations by providing methods and systems for improved analysis of labeled biological samples.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
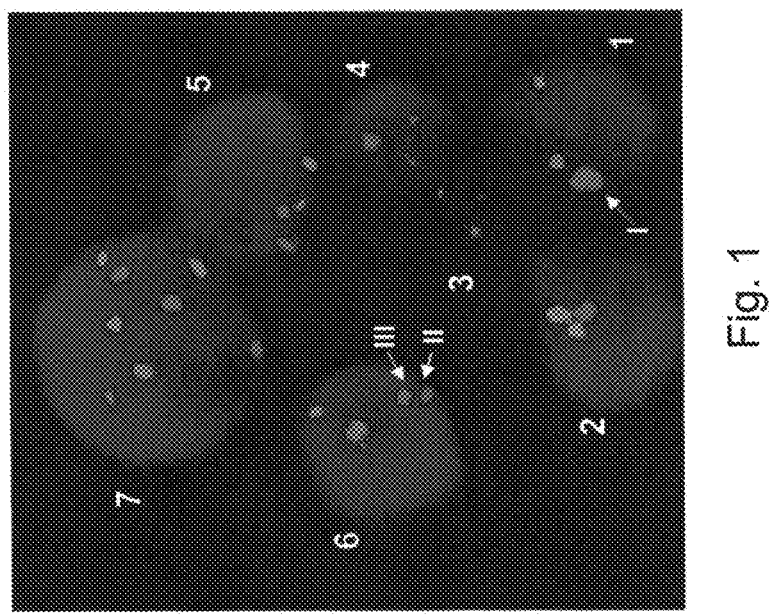

FIG. 1 is a photomicrograph depicting FISH analysis and DAPI counterstaining of a bone marrow sample derived from an acute lymphoblastic leukemia (ALL) patient. FISH was performed using two probes derived from the centromere of chromosome 4 (Green) and the centromere of chromosome 10 (Red). The DAPI counterstaining enables allocating the FISH signal (or spots) to individual cells (the cells are marked with numbers 1-7). Note the presence of one big merged red spot in the nucleus of cell No. 1 (marked by arrow No. I) which is approximately twice the intensity (or area in this particular case) of each of the two single red spots present in cell No. 6 (marked by arrows Nos. II and III).

Figure 2:
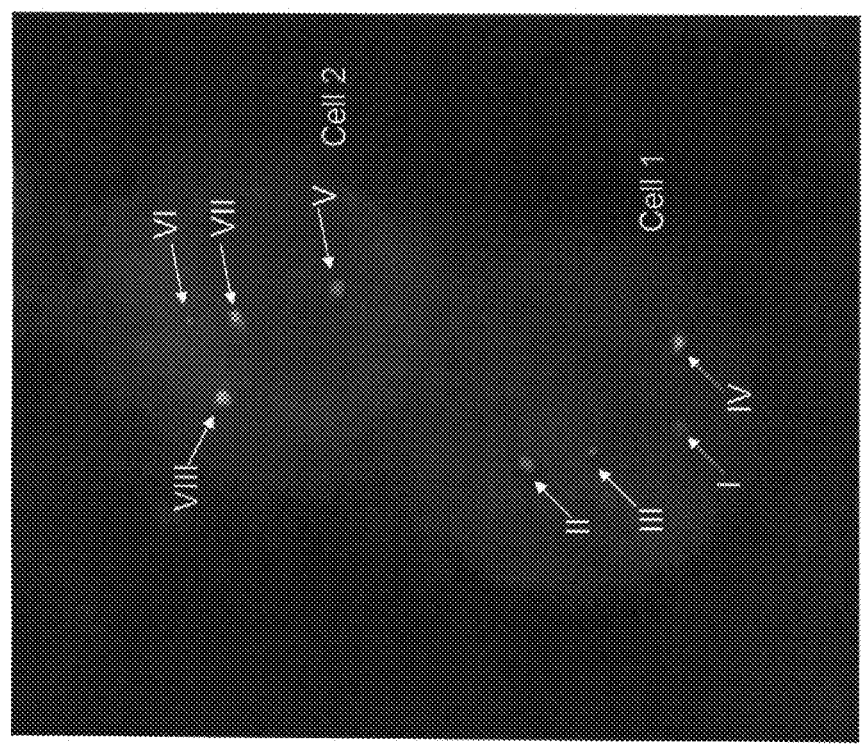

FIG. 2 is a photomicrograph depicting FISH analysis of a bone marrow sample derived from an AML patient harboring the TEL/AML1 fusion gene. FISH was performed using the TEL/AML ES Dual Color Translocation Probe (Vysis). This probe is a mixture of the LSI TEL probe, labeled with SpectrumGreen™, and the AML1 probe, labeled with SpectrumOrange™. The TEL probe begins between exons 3-5 and extends approximately 350 kb towards the telomere on chromosome 12. The approximately 500 kb AML1 probe spans the entire AML1 gene on chromosome 21. Shown are two FISH stained cells (cell 1 and cell 2) with green, red and yellow-orange fluorescent signals. Note the presence of one green fluorescent signal (native TEL; arrow No. I in cell 1 and arrow No. VIII in cell 2), one large red fluorescent signal (native AML1; arrow No. II in cell 1 and arrow No. V in cell 2), one smaller red fluorescent signal (residual AML1; arrow No. III in cell 1 and arrow No. VI in cell 2) and one fused red/green fluorescent signal (yellow-orange; arrow No. IV in cell 1 and arrow No. VII in cell 2), demonstrating the presence of the TEL/AML fusion gene.

Figure 3B:
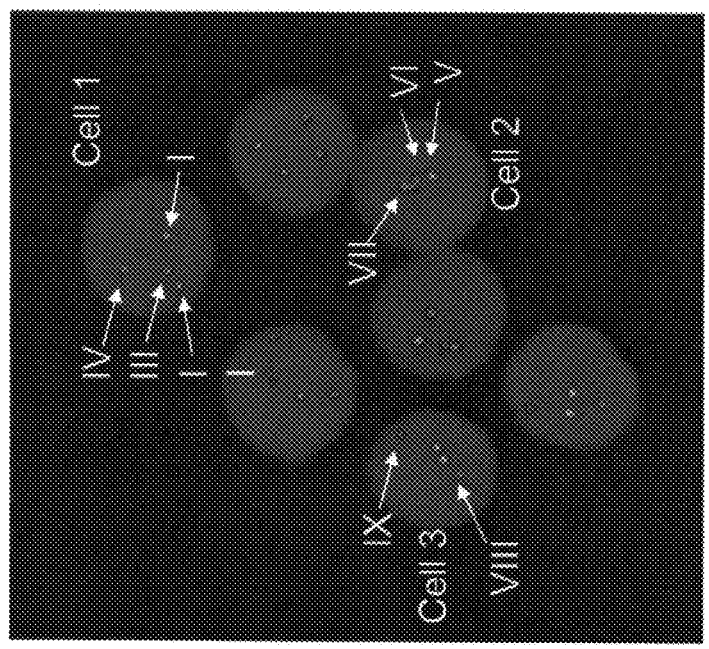
Figure 3A:
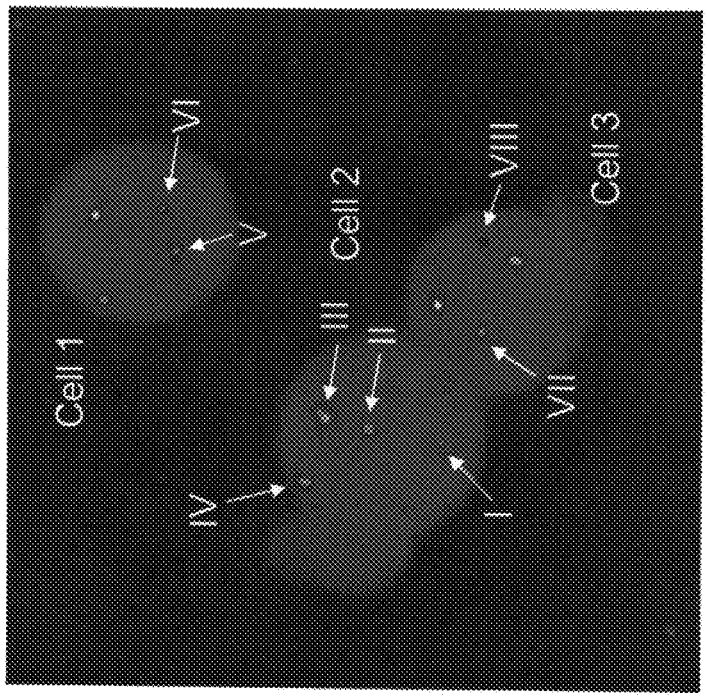

FIGS. 3a-b are photomicrographs depicting FISH analysis of bone marrow samples derived from an AML patient harboring the TEL/AML1 fusion gene (FIG. 3a) and from a normal individual (FIG. 3b). FIG. 3a—Shown are three FISH stained cells (cell 1, cell 2 and cell 3) with green, red and yellow-orange fluorescent signals. Note the presence of one green fluorescent signal (native TEL; arrow No. IV in cell 2), one large red fluorescent signal (native AML1; arrow No. II in cell 2), one smaller red fluorescent signal (residual AML1; arrow No. I in cell 2) and one fused red/green fluorescent signal (yellow-orange; arrow No. III in cell 2), demonstrating the presence of the TEL/AML fusion gene which results from the 12p13/21q22 translocation. Also note the low intensity fluorescent signal of the red spot shown by arrow No. VI in cell 1 as compared to that shown by arrow No. V in cell 1, as well as the low intensity fluorescent signal of the red spot shown by arrow No. VIII in cell 3 as compared to that shown by arrow No. VII in cell 3. FIG. 3b—Shown are FISH stained cells (e.g., cell 1 and cell 2) with green and red fluorescent signals. Note that while in cell 1 there are two red spots (marked with arrows Nos. III and IV) and two green spots (marked with arrows Nos. I and II) demonstrating normal FISH stained chromosomal pattern, in cell 2 the two red signals merged and formed one big red spot (marked with arrow No. VII), which corresponds to the intensity of two individual red spots (e.g., spots III and IV).

Figure 4:
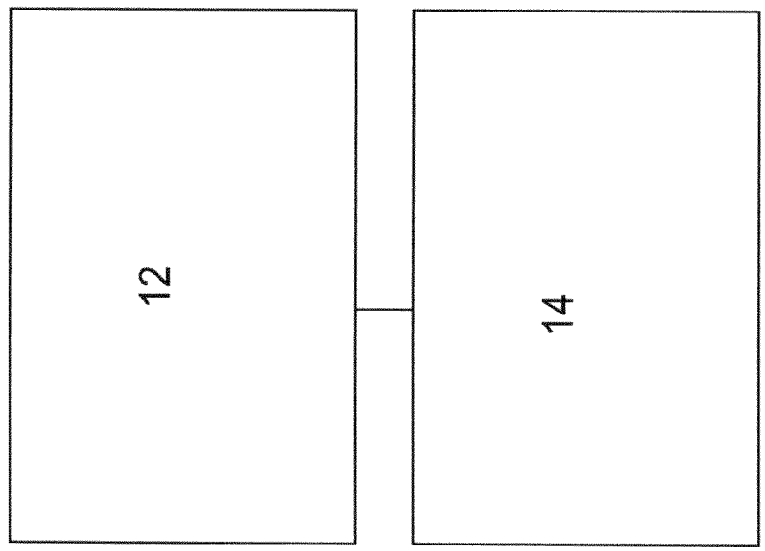

FIG. 4 is a schematic illustration depicting one embodiment of the computer-controlled imaging system of the present invention.

FIG. 5 is a schematic illustration depicting another embodiment of the computer-controlled imaging system of the present invention.

DESCRIPTION OF THE PREFERRED EMBODIMENTS

The present invention is of methods, computer readable storage media and systems which can be used for analyzing labeled biological samples, identifying chromosomal aberrations, identifying genetically abnormal cells and/or computationally scanning the samples using randomly or randomized scanning methods. Specifically, the present invention can be used to analyze FISH-stained samples and automatically identify chromosomal aberrations associated with abnormal intensity ratio of stained occurrences.

The principles and operation of the methods, computer readable storage media and systems according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Analysis of labeled (e.g., stained) biological samples is widely used in both research and clinical applications for the diagnosis of viral infections, inflammation, cancer and/or genetic diseases. For example, in genetic analysis chromosome specimens are stained with chromosomal-specific nucleic acid probes (e.g., FISH probes) capable of detecting chromosomal aberrations such as deletions, duplications and translocations. In most cases, such analyses utilize means for image capture such as a microscope set up connected to a camera and an image analysis software for automated scanning of regions-of-interest (ROIs) in the sample and interpretation of signals (e.g., occurrences of stain such as spots) in the image. The currently used routines for automated detection of chromosomal aberrations include counting the number of stained spots, which encompass pixels above a certain threshold, in each of the analyzed cells. However, several genetic abnormalities such as sub-deletions or translocations, which result in faint or split signals, can be mis-diagnosed using these methods and systems.

While reducing the present invention to practice, the present inventors have uncovered that the relative amount of a label (e.g., stain) having at least two occurrences in the sample is highly valuable for the accurate analysis of the biological sample and particularly, stained chromosomal specimens.

As is shown in FIGS. 2 and 3a-b and is described in Example 2 of the Examples section which follows, by comparing the amount of stains of a nucleic acid probe (e.g., having two occurrences in the sample) so as to obtain the relative amount of the stain and preferably further correlating the relative amount thus obtained to a predetermined translocation ratio, a correct diagnosis of translocation can be automatically achieved. In addition, as is shown in FIGS. 1a-b and is described in Example 1 of the Examples section which follows, using the method of the present invention merged spots resulting from technical difficulties can be automatically divided based on the relative amount of stain in each spot (i.e., occurrence) of the sample.

Thus, according to one aspect of the present invention there is provided a method of analyzing a labeled biological sample. The method is effected by measuring a relative amount of at least one label having at least two occurrences in the labeled biological sample, thereby analyzing the labeled biological sample.

The phrase "labeled biological sample" refers to any biological sample which is labeled with at least one label as is further described hereinbelow. The phrase "biological sample" refers to a sample of a tissue, a cell or a fluid isolated from a subject (e.g., a human being, an animal or a plant). Non-limiting examples of biological samples which can be used along with the present invention include a blood sample (e.g., blood cells, serum and plasma), urine sample, tissue biopsy, tumor biopsy, spinal fluid aspirate [e.g., cerebro spinal fluid (CSF)], bone marrow sample, lymph fluid, the external section of the skin, respiratory, intestinal, and/or genitourinary tract, tears, saliva, sputum, milk, tumor, neuronal tissue, organ, a fetal sample such as amniotic fluid, chorionic villi sample (CVS), maternal blood, cord blood, and a sample of in vivo cell culture constituents. It will be appreciated that the biological sample of the present invention can be in a form of a smear (i.e., when a sample is smeared on a microscopic slide), a cytospin (when the sample which contains cells is centrifuged using a cytospin centrifuge to form a concentrated spot of cells on the microscopic slide) or it can be in a form of a tissue section (e.g., a paraffin section of a cryosection). Thus, the biological sample of the present invention can be processed (e.g., isolated, centrifuged, fixed, sectioned and the like) and labeled according to the required application. For example, the biological sample can be a chromosome specimen derived from fetal or adult cells.

The term "label" as used herein refers to an identifiable substance enabling the identification of a specific moiety of the sample. The label of the present invention can be a stain such as a chromogenic dye, a silver grain (e.g., resulting from photographic emulsion), a luminescent agent such as radioluminescent, chemiluminescent, bioluminescent and photoluminescent (including fluorescent and phosphorescent) as well as a non-color label such as a radioactive signal or a magnetic signal.

Moieties which can be identified using the label of the present invention can be biomolecules such as for example, nucleic acids (i.e., DNA or RNA), amino acids (i.e., polypeptides), carbohydrates, lipids, minerals, vitamins and toxins. Specifically, in a cell- or tissue-containing sample, the label can identify whole cells, connective tissues (using e.g., Aniline Blue WS in Mallory's staining, Fast Green FCF), vasculature or blood cells (using e.g., Neutral Red, Wright's Stain), bone marrow cells (using e.g., MayGrunwald-Giemsa Stain), as well as any cell sub-structure (e.g., organelle) or portions thereof (e.g., chromosomes) such as membrane (using e.g., the Live/Dead kit from Molecular Probes), nucleus (using e.g., Toluidine Blue O, Hematoxylin), nucleoli (using e.g., Hematoxylin), cytoplasm (using e.g., Eosin B), mitochondria (using e.g., DIOC6 stain or modified Gomori trichrome stain), endoplasmic reticulum [using e.g., FX Alexa Fluor 488 Endoplasmic Reticulum Labeling Kit (Invitrogen-Molecular Probes)], Golgi apparatus [using e.g., Anti-golgin-97 or Fluorescent ceramide conjugates (Invitrogen-Molecular Probes)], glycosylated proteins and lipids [using e.g., Lectin conjugates such as Alexa Fluor, TMR (Invitrogen Molecular Probes)], lysosomes [using e.g., the LysoTracker Red DND-99 (Invitrogen-Molecular Probes)], peroxisomes [using e.g., the SelectFX Alexa Fluor 488 Peroxisome Labeling Kit (S34201); (Invitrogen-Molecular Probes)] and the like. Stains such as 4',6-diamidino-2-phenylindole (DAPI), 4',6-bis-2'-imidazolinyl 4H-5H (DIPI), Ethidium Bromide, which bind to DNA can be used to identify cell nuclei. In addition, in chromosome specimens such as interphase, metaphase or prophase nuclei, the stain of the present invention can label specific chromosomes or portions thereof (e.g., using a centromeric probe, a short or long arm—specific probe, a telomeric probe or a whole chromosome painting probe).

The label of the present invention can be conjugated or incorporated to a probe such as a nucleic acid probe or a polypeptide probe (e.g., an antibody or a protein-interacting molecule) capable of binding to specific moieties in the sample For example, the label can be incorporated to the probe during synthesis [e.g., during DNA polymerization using, for example, DIG-11-dUTP, Biotin-16-dUTP] or can be covalently conjugated to the probe using e.g., solid phase synthesis. Specifically, such labels can be, for example, fluorescent molecules (e.g., fluorescein or Texas Red), radioactive molecule (e.g., $^{32}P$-$\gamma$-ATP or $^{32}P$-$\alpha$-ATP), magnetic particles and/or chromogenic substrates (e.g., Fast Red, BCIP/NBT). Alternatively, the probe can be unlabeled but rather detected by a labeled secondary molecule (indirect labeling). For example a probe can be conjugated to a non-labeled tag molecule such as an enzyme [e.g., alkaline phosphatase, horse radish peroxidase (HRP)], biotin, digoxigenin (DIG), hapten and the like, and be further detected using a labeled secondary molecule such as an antibody (e.g., FITC-labeled anti-DIG antibody), a specific-interacting protein (e.g., Texas-Red-labeled avidin or alkaline phosphatase-conjugated streptavidin) or a labeled substrate (e.g., Fast Red for alkaline phosphatase or NBT-BCIP for HRP). Methods of detecting specific nucleic acid sequences (DNA, RNA) using e.g., FISH analysis, RNA-in situ hybridization, in situ RT-PCR or detecting specific amino acids sequences (proteins) sequences using e.g., immunohistochemistry are further described hereinunder.

As mentioned, the method of this aspect of the present invention makes use of a label having at least two occurrences in the sample. It will be appreciated that in the case of a cell- or a tissue-containing sample such at least two occurrences can be either in the same cell or in different cells of the sample.

As used herein the phrase "relative amount of at least one label" refers to an amount of a label at one occurrence in the sample as compared to an amount of the same label at another occurrence in the sample (i.e., a ratio of the amount of label between two occurrences). It will be appreciated that the other occurrence of the label in the sample can also be an average amount of the label as calculated over several or all occurrences in the sample.

Measuring the relative amount of the label can be performed using various techniques known in the art, depending on the type of label used.

For example, when the label is a dye-based stain (e.g., a fluorescent dye), the relative amount can be measured by a spectrometer. A spectrometer is an apparatus designed to accept light, to separate (disperse) it into its component wavelengths, and to measure the light's spectrum, that is the intensity of the light as a function of its wavelength. The relative amount of the dye-based stain of the present invention is preferably measured by an imaging spectrometer, i.e., a spectrometer that collects incident light from a scene and measures the spectra of each picture element (e.g., pixel) thereof. Preferably, the relative amount of the dye-based stain of the present invention is measured by spectral imaging which combines high resolution spectroscopy and high resolution imaging (i.e., spatial information). A non-limiting example of a suitable spectrometer which can be used along with the present invention is the automated image analyzer DISCOVERY® (BECTON DICKINSON IMAGE CYTOMETRY SYSTEMS).

Thus, when using a dye-based stain (e.g., a fluorescent dye), measuring the relative amount of the stain at one occurrence of the sample is preferably effected by measuring the intensity of light (in a portion of or all wavelengths comprising the light) in all pixels encompassing the one occurrence of the stain and comparing such intensity to the intensity of stain measured in another occurrence of the stain (e.g., to an average intensity of several occurrences).

As is mentioned hereinabove, the label of the present invention can also be a radioactive-based or magnetic-based label, i.e., a radioactive or magnetic particle which is conjugated to the probe used to label the sample. The amount of such a label can be measured using any suitable device such as a radioactive measuring device or a magnetic measuring device, capable of detecting a radioactive radiation or a magnetic field, respectively. It should be noted that the radioactive or the magnetic particles used by the method according to this aspect of the present invention should have predetermined radioactive or magnetic properties which are distinguishable from those of the environment in which the sample is analyzed (e.g., the microscope, the camera, the computer).

Once the relative amount of the label is measured it is preferably further correlated with an amount index.

As used herein the phrase "amount index" refers to a ratio (i.e., number) which is indicative of a biological phenomenon (e.g., translocation). The amount index of the present invention can be determined theoretically or preferably, empirically, such as by using the above methodology using well characterized samples. For example, the amount index used by the method according to this aspect of the present invention can be determined for a certain label in either "normal samples" (i.e., biological samples including normal cells, tissues or a-cellular moieties which are obtained from "control" subjects as described hereinunder) or from "abnormal samples" (i.e., biological samples including abnormal cells, tissues or a-cellular moieties which are obtained from affected or carrier individuals).

As used herein the phrase "frequency index" refers to a number of occurrences which is indicative of a biological phenomenon (e.g., trisomy, monosomy). The frequency index of the present invention can be determined theoretically or preferably, empirically, or can be already known for well-characterized probes and/or kits.

The teachings of the present invention can be used to analyze labeled biological samples and detect for example, chromosomal aberrations and/or alternative splicing in cells of the sample. It will be appreciated that such analysis can involve comparing the relative intensity of a label between a "control sample" (i.e., a sample derived from a normal subject, an un-affected subject and/or a subject representing in its genetic and/or biochemical characteristic the majority of the population) and a "test sample" [i.e., sample derived from an affected subject (such as a subject with a pathology) and/or a subject with unknown genetic and/or biochemical characteristic].

For example, the method of the present invention can be used to detect abnormal alternative splicing in cells of the sample. In this case, the amount index can be determined for a label conjugated to a probe capable of detecting alternative splicing of a certain gene. Such a probe can be, for example, a labeled cDNA probe (labeled using e.g., fluorescein or conjugated to Digoxigenin) capable of specifically hybridizing to an mRNA transcript encoding all exons of the gene (referred to as "full-length mRNA transcript" hereinafter). In samples containing only normal cells, which express the full-length mRNA transcript, the relative amount of the label in one cell as compared to another cell is expected to be about 1 (e.g., a value of "1" in the amount index). On the other hand, in samples containing some abnormal cells which express splice variants of the gene such as an mRNA transcript in which at least one exon or a portion thereof is excluded from the transcript (e.g., exon skipping) or an mRNA transcript in which an intronic sequence is transcribed as part of the mRNA (e.g., a readthrough intron), the relative amount of the label in a cell expressing the splice variant as compared to the amount of the label in another cell expressing the full-length mRNA transcript can be for example 0.8 (in case of exon skipping, demonstrating loss of 20% of the amount of label) or 1.1 (in case of a readthrough intron, demonstrating an addition of 10% of the amount of label), respectively. It will be appreciated that the amount index can be determined based on several samples with known expression patterns. For example, a value of "1" represents full-length transcript, a value of "0.8" represents a specific exon skipping and a value of "1.1" represents a specific readthrough intron. Thus, when an unknown sample is analyzed, the ratio obtained by dividing the amount of label in one cell to that of another cell (or an average cell) can be easily compared to the amount index, and a presence of a specific ratio is indicative of a specific expression pattern (e.g., exon skipping, readthrough intron or full-length transcript).

It will be appreciated that in case of a biological sample having all cells expressing only one splice variant such as the exon skipping variant, measuring the relative amount of label in all occurrences of such a label in the biological sample may falsely result in a value of "1" which is indicative of a full-length transcript as described hereinabove. To overcome such a possible limitation, the method according to this aspect of the present invention preferably measures the amount of label in two occurrences of the sample wherein each occurrence is derived from a different biological sample. For example, one occurrence can be derived from a "control" subject and the other can be derived from a "test" subject. Using such a configuration it would be easy to identify biological samples which are "homozygous" to an abnormal expression pattern (e.g., alternative splicing) or chromosomal pattern (e.g., homozygosity to a deletion).

As is mentioned hereinabove, the biological sample of the present invention can be a chromosome specimen in different stages of the cell cycle such as interphase, metaphase, prophase, anaphase or telophase and the label used to analyze the sample can be a nucleic acid probe capable of specifically binding a chromosome or a portion thereof (e.g., a FISH probe).

It is well known in the art that an abnormal number of FISH occurrences (e.g., stained spots) in cell nuclei can indicate the presence of chromosomal aberrations. For example, the presence of three chromosome 21 occurrences per nucleus indicates the presence of trisomy 21 (Down syndrome). However, in many cases, the frequency of FISH occurrences can be normal (i.e., as expected, usually 2 occurrences of a certain chromosomal probe in a single nucleus), yet the sample can include chromosomal aberrations such as sub-deletions or translocations.

It will be appreciated that chromosomal aberrations such as deletions or translocations can be identified by measuring the relative amount, and optionally a frequency of at least one label of a nucleic acid probe in the sample.

As used herein the phrase "chromosomal aberration" refers to any change or deviation between the structure (including nucleic acid sequence) and/or number of the subject chromosome or karyotype and a normal (i.e., "non-aberrant") homologous chromosome or karyotype. The terms "normal" or "non-aberrant," when relate to chromosomes or karyotypes, refer to the predominate karyotype, banding and/or structure pattern (including nucleic acid sequence) found in healthy (e.g., un-affected) individuals of a particular species and gender. Non-limiting examples of chromosomal aberrations which can be detected by the method according to this aspect of the present invention, include aneuploidy (a loss or a gain of chromosomes), inversion, translocation [e.g., balanced or imbalanced (or unbalanced) translocations], deletion (including sub-deletion and micro-deletion), duplication, subtelomeric rearrangement, unbalanced subtelomeric rearrangement, and telomere instability and/or shortening.

It will be appreciated that chromosomal aberrations are highly associated with various pathologies. For example, the Tel/AML1 fusion gene which involves a translocation between chromosome 12p13 to chromosome 21q22 can be found in 25% of children with acute lymphoblastic leukemia (ALL; Golub, T. R., et al., Proc. Natl. Acad. Sci. U.S.A. 92: 4917-4921, 1995) and the CBFB/MYH11 fusion gene which involves inversion Inv(16)(p13; q22) is found in almost all cases of acute myeloid leukemia (AML M4Eo) (Kundu M., et al., Blood. 2002; 100: 2449-56).

As used herein the phrase "nucleic acid probe" refers to any polynucleotide which is capable of specifically hybridizing to a target nucleic acid sequence (e.g., chromosomal DNA) present in the specimen of the present invention (e.g., the metaphase or interphase nuclei). Such a polynucleotide probe can be at any size, including short polynucleotides [e.g., 5 kilobase pairs (kbp)], intermediate size polynucleotides (e.g., 40 kbp) and/or long polynucleotides (e.g., 400 kbp).

According to preferred embodiments of the present invention the nucleic acid probe used by the present invention can be any directly or indirectly labeled DNA molecule such as bacterial artificial chromosome (BACs), P-1 artificial chromosomes (PACs), chromosomal libraries, whole chromosomal DNA and/or any portion of a chromosomal DNA.

For certain applications such as Quantitative FISH, the probe is preferably a DNA analogue such as a peptide nucleic acid (PNA) probe. PNA probes are synthetic DNA mimetics in which the sugar phosphate backbone is replaced by repeating N-(2-aminoethyl) glycine units linked by an amine bond and to which the nucleobases are fixed (Pellestor F and Paulasova P, 2004; Chromosoma 112: 375-380). Thus, the hydrophobic and neutral backbone enables high affinity and specific hybridization of the PNA probes to their nucleic acid counterparts (e.g., chromosomal DNA). Such probes have been applied on interphase nuclei to monitor telomere stability (Slijepcevic, P. 1998; Mutat. Res. 404:215-220; Henderson S., et al., 1996; J. Cell Biol. 134: 1-12), the presence of Fanconi aneamia (Hanson H, et al., 2001, Cytogenet. Cell Genet. 93: 203-6) and numerical chromosome abnormalities such as trisomy 18 (Chen C, et al., 2000, Mamm. Genome 10: 13-18), as well as monosomy, duplication, and deletion (Taneja K L, et al., 2001, Genes Chromosomes Cancer. 30: 57-63).

As is mentioned hereinabove, the nucleic acid probe can be directly or indirectly labeled using various labels. According to preferred embodiments of this aspect of the present invention, the nucleic acid probe is a FISH probe which is labeled with a fluorescent dye such as FITC, SpectrumOrange™, SpectrumGreen™, Cy3, Texas Red, Cy5, Aqua, Gold and Cy5.5.

Following is a non-limiting list of staining methods which can be used to stain specific nucleic acid sequences (DNA, RNA) or amino acid sequences (proteins) of the biological samples of the present invention.

FISH—FISH analysis is usually performed on interphase chromosomes. Briefly, directly-labeled probes [e.g., the CEP X green and Y orange (Abbott cat no. 5J10-51)] are mixed with hybridization buffer (e.g., LSI/WCP, Abbott) and a carrier DNA (e.g., human Cot 1 DNA, available from Abbott). The probe solution is applied on microscopic slides containing cells (e.g., fetal cells) and the slides are covered using a coverslip. The probe-containing slides are denatured for 3 minutes at 70° C. and are further incubated for 48 hours at 37° C. using an hybridization apparatus (e.g., HYBrite, Abbott Cat. No. 2J11-04). Following hybridization, the slides are washed for 2 minutes at 72° C. in a solution of 0.3% NP-40 (Abbott) in 60 mM NaCl and 6 mM NaCitrate (0.4×SSC). Slides are then immersed for 1 minute in a solution of 0.1% NP-40 in 2×SSC at room temperature, following which the slides are allowed to dry in the dark. Counterstaining is performed using, for example, DAPI II counterstain (Abbott).

High-Resolution Multicolor Banding (MCB) on Interphase Chromosomes—

This method, which is described in detail by Lemke et al. (Am. J. Hum. Genet. 71: 1051-1059, 2002), uses YAC/BAC and region-specific microdissection DNA libraries as DNA probes for interphase chromosomes. Briefly, for each region-specific DNA library 8-10 chromosome fragments are excised using microdissection and the DNA is amplified using a degenerated oligonucleotide PCR reaction. For example, for MCB staining of chromosome 5, seven overlapping microdissection DNA libraries were constructed, two within the p arm and five within the q arm (Chudoba I., et al., 1999; Cytogenet. Cell Genet. 84: 156-160). Each of the DNA libraries is labeled with a unique combination of fluorochromes and hybridization and post-hybridization washes are carried out using standard protocols (see for example, Senger et al., 1993; Cytogenet. Cell Genet. 64: 49-53).

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Immunohistochemical Analysis:

This method involves detection of a substrate in situ in fixed cells by substrate specific antibodies. The substrate specific antibodies may be enzyme linked or linked to fluorophores (as in the case of immunofluorescence). Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxylin or Giemsa stain.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

Thus, in order to identify a chromosomal aberration according to this aspect of the present invention the relative amount of at least one label of a nucleic acid probe (e.g., a FISH probe) is measured.

For example, as is shown in FIGS. 3a-b and is described in Example 2 of the Examples section which follows, in order to identify a translocation such as the TEL/AML1 fusion gene (ETV6/RUNX1 re-arrangement) using the LSI TEL (labeled with SpectrumGreen™) and AML1 (labeled with SpectrumOrange™) FISH probes, the relative intensity of the SpectrumOrange™ fluorescence is measured in an occurrence in the sample (i.e., in a SpectrumOrange™-stained occurrence). Since in a sample harboring cells with the TEL/AML1 translocation there are two groups of SpectrumOrange™-occurrences with distinct intensities, i.e., a group of occurrences with high intensity (corresponding to non-translocated chromosomes, referred to as "high intensity group" hereinafter) such as spots No. II (in cell 2, FIG. 3a), V (in cell 1, FIG. 3a) and VII (in cell 3, FIG. 3a), and a second group of occurrences with low intensity (corresponding to aberrant chromosomes due to translocation, referred to as "low intensity group" hereinafter) such as spots No. I (in cell 2, FIG. 3a), VI (in cell 1, FIG. 3a) and VIII (in cell 3, FIG. 3a), the intensity of any of the analyzed SpectrumOrange™-occurrences in the sample can be compared to either the average intensity of the "high intensity group" or to the average intensity of the "low intensity group". Alternatively, the intensity of any of the analyzed SpectrumOrange™-occurrences in the sample can be compared to the intensity of any other SpectrumOrange™-occurrences in the sample or to the average intensity of all SpectrumOrange™-occurrences spots in the sample. It will be appreciated that the average intensity of occurrences can be determined using a portion of the occurrences and it is within the capabilities of those skilled in the art to determine the minimal and/or optimal number of occurrences needed for determining such average intensity.

As mentioned the frequency of the label of the nucleic acid probe can be determined on top of the relative amount thereof. This may shed light on chromosomal aberrations related to an abnormal copy number of chromosomes such as polyploidy.

Preferably, the number of occurrences of the label (e.g., the number of FISH-stained spots) is determined in a single cell of the sample. It will be appreciated that determination of which occurrence of a label (e.g., a spot) is associated with a certain cell is well within the capabilities of one skilled in the art. For example, one can utilize an additional stain capable of specifically labeling the cell nucleus (e.g., a DAPI stain) to thereby localize each occurrence of the stain (e.g., a red FISH stain) to a certain cell nucleus. Briefly, the number of occurrences of one stain (e.g., red) in the sample is calculated per each of the stained nuclei (e.g., DAPI-stained nuclei).

Thus, using the teachings of the present invention (i.e., measuring the relative amount of label and optionally also the frequency of the label) it is possible to clearly identify chromosomal aberrations such as translocations or sub-deletions which could have been mis-diagnosed using prior art approaches. For example, if the cell nuclei shown in FIGS. 3a-b were analyzed using prior art approaches, i.e., by only counting the number of SpectrumOrange™ and/or SpectrumGreen™—occurrences in each cell nuclei, the translocation present in the nucleus of cell 2 of FIG. 3a could have been mis-diagnosed since the frequency of SpectrumOrange™ occurrences in that nucleus is 2, as expected from a normal nucleus.

Preferably, the relative intensity of the label measured according to this aspect of the present invention is correlated with the amount index. The amount index according to this aspect of the present invention can be prepared for each label capable of detecting a certain chromosomal aberration such as a deletion [e.g., microdeletion of chromosome 22q associated with Di George/Velocardiofacial syndrome (DGS/VFCS), microdeletion of 15q11-q13 associated with Prader-Willi syndrome (PWS) and Angelman syndrome (AS), a translocation (e.g., the ETV6/RUNX1 re-arrangement, the BCR/abl, the PML/RARA, the AML/ETO) or an inversion (e.g., Inv (16)CBFB). For example, if the chromosomal aberration to be identified according to the present invention is the Di George/Velocardiofacial syndrome (DGS/VFCS), which is associated with a micro-deletion of chromosome 22q11.2 (Kitsiou-Tzeli S, et al., In Vivo. 2004, 18: 603-8), and the nucleic acid probe used by the method of the present invention encompasses a chromosomal DNA derived from chromosome 22q, the relative intensity of a label occurrence having the deleted chromosome as compared to the intensity of a label occurrence having the normal chromosome 22 can be calculated and such a value (i.e., the ratio between such intensities) can form part of the amount index of the present invention. Thus, the amount index can include multiple values, each representing an intensity ratio of a label associated with a specific nucleic acid probe obtained between an aberrant chromosome and a normal chromosome. Once prepared, such amount index is used for comparing the relative amount of label (e.g., intensity ratios) obtained for a specific label between two occurrences of the label (e.g., two stained spots) in the sample.

It will be appreciated that the teachings of the present invention can be further used to identify chromosomal abnormalities or aberrations in genetically abnormal cells. The phrase "genetically abnormal cell" as used herein refers to a cell harboring a chromosomal aberration as described hereinabove.

Identification of genetically abnormal cells according to this aspect of the present invention is effected by measuring in a cell the relative amount and optionally the frequency of at least one label of a nucleic acid probe, wherein the label having at least two occurrences in the sample. Thus, the determination if a cell is genetically abnormal is based on measuring the relative amount of the label in the cell and preferably comparing such relative amount to the amount index as described hereinabove.

Since chromosomal abnormalities or aberrations are a leading cause of pathologies having a genetic basis such as congenital disorders and acquired diseases (e.g., malignancies), the method according to this aspect of the present invention can be further used to diagnose a pathology associated with chromosomal aberration. Non-limiting examples of such pathologies include, leukemia, solid tumor, mental retardation, infertility or multiple miscarriages.

Preferably, the relative amount of the label and optionally also the frequency of the label is measured for several cells of the sample such as for a representative number of cells in the sample, and the percentage of genetically abnormal cells is determined. For example, a sample can include only a few genetically abnormal cells (e.g., as in the case of low percentage of mosaicism or in a sample including a low percentage of cancerous cells such as a bone marrow sample), a large portion of genetically abnormal cells (e.g., in the case of high percentage of mosaicism or high percentage of cancerous cells) or can include only genetically abnormal cells such as in the case of a congenital disorder affecting all germ line cells or a sample derived from e.g., a solid tumor.

In several pathologies such as congenital disorders characterized by mosaicism [e.g., trisomy 21 (Down syndrome) or XO (Turner's syndrome)] the frequency of the abnormal cells is indicative of the possible outcome of having the genetically abnormal cells. For example, in Down syndrome, a direct relationship between the percentage of trisomic cells and the degree of phenotypic manifestations was shown (Modi D, et al., 2003, Reprod. Biomed. Online. 6: 499-503). Thus, the present invention envisages determining the prognosis of a pathology associated with chromosomal aberrations by measuring the frequency of the genetically abnormal cells in the sample.

It will be appreciated that the teachings of the present invention can be also used to classify existing nucleic acid probes or kits containing same according to amount indexes prepared for each nucleic acid probe and the respective chromosomal aberration identified therewith. For example, the amount index for identifying the TEL/AML1 translocation using the TEL/AML1 ES Dual Color Translocation Probe available from Vysis, is a value of 0.2-0.4 with respect to the SpectrumOrange™ stain. Such classification enables the use of a variety of known nucleic acid probes and/or kits according to the method of the present invention.

It will be appreciated that in certain cases, the labeled biological sample may be labeled in a manner which does not allow its immediate classification (e.g., healthy or affected cell) based on a known or expected pattern of labeling. For example, in case the biological sample includes FISH stained chromosomes using three probes (each corresponding to a different chromosome), the expected pattern of labeling in a normal cell will be of 2 dots (occurrences) of each of the probes (labels). On the other hand, the expected pattern of labeling in a trisomy-associated cell will be 2 dots of each of the first two probes and 3 dots of the third probe. In this case, an unexpected pattern of labeling may be, for example, a presence of 2 dots of the first probe (first label), 4 dots of the second probe (second label) and absence of dots of the third probe (third label). Alternatively, another unexpected pattern of labeling may be, for example, a presence of 2 dots of each of the 3 labels corresponding to the probes used and an additional dot of a forth label, which does not correspond to any of the used probes. The latter example may result, for example, from an artifact of the staining method (e.g., technical difficulties).

While further reducing the present invention to practice, the present inventors have uncovered that objects of biological samples can be analyzed based on the differences from a known reference object.

Thus, according to yet another aspect of the present invention, there is provided a method of analyzing a labeled biological sample. The method is effected by: (a) sorting at least one non-classified object of the biological sample according to a difference from a classified object-of-interest; and (b) signaling a signal to alert a detection of the difference; thereby analyzing the labeled biological sample.

The term "object" as used herein refers to any labeled moiety (as described hereinabove) which is present in the biological sample. Examples include, but are not limited to, biomolecules, whole cells, portions of cells such as various cell components [e.g., a sub-cellular organelle such as cytoplasm, mitochondria, nucleus (e.g., chromosomes), nucleoli, nuclear membrane, cell membrane, Golgi apparatus, lysosomes, and the like] and/or a cell secreted components such as proteins which are secreted to the intercellular space, proteins secreted to the body fluids such as serum, cerebrospinal fluid, urine and the like.

The phrase "non classified object" refers to an object that exhibits at least one difference in labeling from the classified object-of-interest (e.g., a reference object with known amount and/or number of occurrences of a certain label and/or of all labels used to stain the biological sample). Such a difference can be a difference in the relative amount of a certain label (as described hereinabove) and/or in the number of occurrences of a certain label of the labeled biological sample.

For example, in case a certain label exhibits at least one occurrence in the classified object-of-interest (e.g., a cell with known FISH pattern of certain probes), a difference in the number of occurrences of that label may be the presence of no occurrences at all (absence of a certain label in the non-classified object) or a presence of a number of occurrences in the non-classified object which is different from that of a classified object. For example, if the classified object is a cell exhibiting 2 occurrences of a FISH probe (2 FISH dots), the non-classified object may exhibit 3 occurrences of the FISH probe (3 FISH dots) or no occurrences of the FISH probe. Another example of a more complex pattern of labeling is of a classified object (e.g., cell) having 2 occurrences of each of three labels (e.g., using three different FISH probes) and a non-classified object having 2 occurrences of the first label (first FISH probe), one occurrence of a second label (second FISH probe) and 2 occurrences of a third label (third FISH probe). In this case, the differences between the classified and non-classified objects relate only to the second label (second FISH probe). In another example, the classified object may exhibit 2 occurrences of each of two labels and the non-classified object may exhibit 2 occurrences of each of the first two labels (which are present in the classified object) and an additional occurrence of a third label (which is absent in the classified object), reflecting a combination of the first two labels (e.g., orange, which results from red and yellow).

Preferably, the non-classified object comprises a plurality of non-classified objects.

Preferably, the difference is a minimal difference from the classified object-of-interest. As used herein the phrase "minimal difference" refers to the smallest difference between one non-classified object (out of the plurality of non-classified objects) and the classified object-of-interest. Accordingly, the non-classified object with the minimal difference is the object which is most similar to the object-of-interest.

According to the method of this aspect of the present invention the difference (even a minimal difference) between the classified and the non-classified objects is highlighted so as to inform on the presence of such a difference. It will be appreciated that when using an automated image analysis system (as is further described hereinbelow), highlighting of the difference can be effected using, e.g., a flickering label (e.g., of the same color as the label with the detected difference) which informs the user of the presence of such a difference.

Preferably, sorting the non-classified object further comprises generating a similarity index. As used herein the phrase "similarity index" refers to a list or a key wherein a difference is assigned to each of the non-classified objects. It will be appreciated that the non-classified objects can be scored according to the degree of differences as compared to the classified object (e.g., from the minimal difference to the maximal difference). For example, a non-classified object with the minimal difference may be on the top of the list and the non-classified object with multiple differences or maximal difference(s) can be at the bottom of the list.

The similarity index may also include a distinguishable signal (e.g., a color index) which corresponds to the specific difference. For example, if the difference in a non-classified object involves a difference in the relative amount (intensity) or number of occurrences of a certain label (e.g., yellow), then the distinguishable signal of that difference may be a yellow color. Thus, in the similarity index a plurality of distinguishable signals (e.g., colors such as yellow, green, red or Aqua) is assigned to a plurality of differences, and preferably each the distinguishable signals corresponds to the specific difference (e.g., if the difference is in a FISH probe labeled in red, then the distinguishable signal will be a red color). It will be appreciated that marking a non-classified object with a certain distinguishable signal (e.g., yellow) may indicate on a biological phenomenon (e.g., translocations, deletions, insertions) as well as on technical difficulties resulting in the appearance of certain differences between the objects of the biological sample.

The above described methodology is preferably effected using automatic systems which allow the qualification of large numbers of specimens and therefore are more suitable for clinical applications.

Indeed, as is mentioned in the background section hereinabove, in most research and clinical applications analysis of stained biological samples is performed using image analysis systems, and in most cases using computer-controlled image analysis systems. In such systems the samples are automatically scanned by controlling the movement of the stage on which the sample is place. Such scanning can include the entire sample or only selected parts of the sample [i.e., parts comprising the regions of interest (ROI)]. Selection of ROIs is crucial for accurate diagnosis of biological samples in which the biological moieties of interest (e.g., cells) are not evenly distributed on the slide. This is of particular importance in cases of samples with mixed cell population such as tissue biopsies with cancerous and non-cancerous cells, maternal-derived fetal cells, bone marrow and/or blood samples and/or samples with genetic mosaicism in which only part of the cells exhibit a certain chromosomal abnormality. While the currently practiced methods of scanning the ROIs begin with the center of slide and proceed in a circular manner outward, moving from one ROI to an adjacent one, in many cases scanning may begin with an area that is completely irrelevant for analysis thus resulting in either mis-diagnosis due to under-scanned areas or in enormously long scanning times which are impractical for both research and clinical applications.

Thus, while further reducing the present invention to practice, the present inventors have uncovered that computational scanning of a sample can be performed in a randomly or randomized (i.e., partly randomly) manner. As is shown in Example 3 of the Examples section which follows, using the randomly or a randomized scanning methods of the present invention representative ROIs, which cover the entire sample, are scanned in a highly efficient manner.

As used herein the phrase "computationally scanning" refers to a computer-controlled scanning of the sample, i.e., the scanning is performed according to a computer program (e.g., a scanning software) which selects the regions to be scanned. Preferably, the computational scanning of the sample is effected by randomly scanning of the sample.

The phrase "randomly scanning" refers to a scanning mode of a sample which is governed by or is depended on a chance. For example, scanning can begin by selecting a random X and Y coordinates (e.g., $X_1Y_1$) and continue with another random X and Y coordinates (e.g., $X_2Y_2$) which are selected using a statistical distribution function. Such random scanning can exclude already scanned points from being scanned again. As will be appreciated by one of ordinary skill in the art, this method ascertains a random coverage of the scanned region.

Suitable statistical distribution functions which can be used along with the method of this aspect of the present invention include, but are not limited to, a uniform distribution, a Gaussian distribution, a t-distribution and a $\chi^2$ distribution.

In order to ensure better coverage of the whole sample, and to avoid scanning of ROIs which are close by to each other, the computational scanning of the present invention preferably comprises randomized scanning, which is more similar to a cognitive scanning strategy performed manually by an experienced individual skilled in the art.

As used herein "randomized scanning" refers to a scanning in which random selections are combined with deterministic selections. Thus, randomized scanning can refer, for example, to a situation in which one or more picture elements are randomly selected from a set of picture elements which are selected using a predetermined criterion.

A randomized scanning mode according to this aspect of the present invention can be effected by randomly scanning each of the sub-regions of the sample. For example, the relevant sample area can be divided to sub-regions (e.g., 2×2, 2×3, 3×3, 3×4, 4×4, 4×5, 5×5, 3×3 and the like), and the images are scanned by selecting one image at a time from one of the sub-regions, wherein the specific area (i.e., ROI) to be scanned within each sub-region is randomly selected using a statistical distribution function as described hereinabove. It will be appreciated that scanning can be effected on a pre-determined number of images in each of the sub-regions such that a comprehensive scanning is obtained. Once the randomly scanning of the first sub-region is complete (with the pre-determined number of ROIs), the next sub-region is further scanned in a similar manner.

Additionally or alternatively, a randomized scanning according to the method of this aspect of the present invention is preferably effected by sequentially scanning areas being farthest of pre-scanned areas in the sample.

Briefly, one starts at two given points (which can be selected randomly), and then searches by jumping to the point that is farthest away from all the previous points, and continues in the same manner. For example, if a region of 4 cm by 4 cm is to be scanned, the method randomly selects the first two coordinates to be scanned, e.g., $X_1Y_1$ and $X_2Y_2$, and then jumps to a third point, $X_3Y_3$, which is farthest from $X_1Y_1$ and $X_2Y_2$. The next point to be scanned is a forth point $X_4Y_4$ which is farthest from $X_1Y_1$, $X_2Y_2$ and $X_3Y_3$. In such a way the whole slide is scanned with a uniform distribution such that for each given number of frames that are captured, the frames are uniformly distributed in the relevant region.

Thus, the randomized scanning methods of the present invention are more efficient in covering the whole relevant areas of the sample while efficiently scanning it.

As is mentioned before, scanning of the sample is controlled by a data processor (e.g., a computer). Preferably, computationally scanning of the sample is effected by a computer-controlled scanning system capable of acquiring the data from the label of the sample. The phrase "computer-controlled scanning system" refers to any scanning system which is controlled by a computer and is capable of selecting ROIs, acquiring data and analyzing the sample according to appropriate computer programs. The type of scanning system is depended on the type of labeling. Specifically, when the labeling is radioactive the scanning is effected using a radioactive measuring device; when the labeling is by magnetic particles, the scanning is by a magnetic field measuring device; and when the labeling is by a stain, the scanning is effected using an imaging system. It is to be understood that any combination of the above labeling techniques and types of scanning system is not excluded from the scope of the present invention.

According to preferred embodiments of the present invention the computer controlled scanning system comprises a computer and a computer-controlled mechanical stage.

Preferably, when a computer-controlled imaging system is employed, such a system comprises an optical microscope and a digital imaging system.

The optical microscope used by the computer-controlled imaging system of the present invention can be any microscope or microscope set up known in the art which enables optic visualization of magnified small objects present on the biological sample of the present invention. Such optic microscope preferably includes lenses which build the illumination optics (usually in a form of an array), objective lenses (e.g., ×0.5, ×10, ×20, ×40, ×63, ×100, and the like) and/or ocular lenses (e.g., ×10) with distinct magnification power. Preferably, for the detection of fluorescent signals the microscope also includes illumination accessory which produces sharp fluorescent images. Non-limiting examples of a microscopic set up which can be used along with the present invention include, the Eclipse i-series 90i, the Eclipse i-series 80i, Eclipse E600FN physiostation, Eclipse inverted microscopes (e.g., TE2000-E, TE2000-U, TE2000S) available from Nikon, Inc., the Axiostar Plus, Axioskop 40, Axioskop 40 Tetrad, Axioskop 2 FS, Axio Imager, Axiopath, and inverted microscopes such as Axioinvert 40 and Axioinvert 200, available from Zeiss, Inc.

The digital imaging system of the present invention includes means to acquire and process the image. The digital imaging system uses the microscope, with appropriate filters, to magnify the image, an illumination source to view the image and a charge-coupled device (CCD) camera to acquire the image by translating the light into electronic impulses which end up on a video monitor or TV.

The illumination source used by the digital imaging system of the present invention can be any illumination source, including, without limitation, a white light source or a wavelength specific light source, e.g., a UV light source and the like. The filters, which are associated with the microscope, can be filters for bright field application (e.g., using white light) such as a blue filter, a green filter or a brown filter, or for dark field application (e.g., using a UV light) such as fluorescent filters. A typical fluorescent filter set includes an excitation filter, dichromatic beamsplitter (e.g., a mirror), and a barrier (or emission) filter. Excitation filters can be designed to allow light to excite the sample at distinct wavelength such as ultraviolet excitation (e.g., between 330 and 380 nanometers), violet excitation (e.g., between 379-420 nanometers), blue-violet excitation (e.g., between 400-446 nanometers), blue excitation (e.g., between 420 and 495 nanometers), green excitation (e.g., between 510 and 560 nanometers) and/or yellow excitation (e.g., between 532 and 587 nanometers), such as the Epi-fluorescent filters available from Nikon, Inc. or the high efficiency (HE) filter set available from Zeiss, Inc. The filters can be manually or automatically replaced depending on the desire application (e.g., staining with fluorescent probes) by moving the wheels to which they are connected.

As is mentioned in the background section, existing imaging systems currently include either a monochrome camera or a color camera for image capture. While further reducing the present invention to practice, the present inventors have devised a computer-controlled imaging system which can use both a monochrome camera and a color camera which are selected by the computer according to the application and/or stains used. Such selection is preferably performed using a suitable algorithm as is further described hereinunder.

Preferably, the monochrome camera includes a black and white array detector, and the color camera is capable of acquiring, at a single exposure, two or more color channels, more preferably, three color channels, e.g., a red channel a green channel and a blue channel, also known as RGB channels. It is recognized that while the color camera can be used to provide fast imaging and analysis of a relatively small number of stains, the monochrome camera can be used to provide accurate analysis of complicated samples in which the number of stains is large.

Thus, the selection between the monochrome and color cameras is preferable performed in accordance with the sample being imaged.

Generally, but not obligatorily, the color camera is selected when the number of different stains in the sample is smaller than the number of the color channels of the color camera. Representative examples for situations in which the color camera is preferred over the monochrome camera, include, without limitation, bright field and simple (typically 1-3 colors) FISH probes.

Similarly, when the number of different stains in the sample is large (for example, 4 or more different stains), the monochrome camera is used in combination with the aforementioned filters, where a plurality of exposures of the monochrome camera is performed, each time with different filter. This embodiment is particularly useful for assays in which multiple stains are applied to the same slide sequentially in order to detect different features/parameters of the sample. Representative examples for situations in which the monochrome camera is preferred over the color camera include, without limitation, bone marrow or urine samples which are sequentially stained using different protocols.

The CCD camera of the present invention can be any known CCD camera such as the Zeiss FF450 Fundus Camera, the AxioCam HS, the AxioCam MRc5, the AxioCam MR and the AxioCam HR (Zeiss, Inc.).

The computer-controlled mechanical stage is a microscope-associated platform capable of holding the biological sample of the present invention (e.g., in a form of a microscopic slide, a tissue culture flask, a tube and the like) which movement is controlled by a computer program. The mechanical stage used by the present invention is capable of moving along the X, Y and/or Z axes such that ROIs of the biological sample placed thereon can be selected (or scanned). Usually, the computer-controlled mechanical stage is designed to hold several biological samples that are subject for analysis (e.g., 8). Preferably, the movement of the computer-controlled mechanical stage of the present invention is controlled such as to enable randomly and/or randomized computational scanning of the sample essentially as described hereinabove.

The computer used by the present invention is a processing unit with various computer programs which executes sample analysis according to the teachings of the present invention. Specifically, the programs used by the computer of the present invention are designed to execute the method of analyzing labeled biological samples, the method of identifying chromosomal aberrations, the method of identifying genetically abnormal cells, and the method of scanning the sample using randomly or randomized computational scanning. It will be appreciated that in order to execute such methods the computer of the present invention is capable of controlling the movement of the mechanical stage of the microscope, the selection of the monochrome or color camera, the image acquisition parameters of the camera, the selection of light source and intensity, the shutter and the filter wheels (in order to replace filters).

A non-limiting example of the computer-controlled imaging system of the present invention is presented in FIG. 4. Reference is now made to FIG. 4.

System 10 comprises input unit 12 for receiving data of the stained sample; and analyzer 14 associated with input unit 12. Analyzer 14 is for measuring a relative amount and optionally a frequency of at least one stain (e.g., a nucleic acid probe) having at least two occurrences in the sample. The term "analyzer" as used herein refers to any computer processing unit that can analyze the input data received from the input unit of the present invention.

As used herein the phrase "input unit" refers to any device (preferably electronic) that enters image data into the system of the present invention (e.g., a digital imaging system as is further described hereinunder).

A more elaborated configuration of system 10 for identifying chromosomal aberrations in a sample can be devised. Reference is now made to FIG. 5.

System 100 comprises digital imaging system 110, processing unit 122 and mechanical stage 124. Digital imaging system 110 comprises microscope 112, microscope filter(s) 114, microscope illumination source 116, monochrome camera 118 and color camera 120. Digital imaging system 110 preferably acquires and processes images obtained from ROIs in the FISH stained biological sample. The biological sample is preferably analyzed using computer-controlled imaging system 100. First, the biological sample is subjected to computational scanning of the sample using the randomly or randomized scanning methods as further detailed hereinabove. Computational scanning is executed by processing unit 122, which controls the movement of mechanical stage 124 along the X and Y axes in order to select for ROIs in the sample. Unit 122 preferably controls also the movement of mechanical stage 124 along the Z axis in order to obtain maximal focus level of the image of each of the selected ROIs. Digital imaging system 110, as controlled by computer processing unit 122, acquires the best focused images in each ROI. Unit 122 also controls the selection of monochrome camera 118 or color camera 120 used by digital imaging system 110 for image capture. Computer processing unit 122 also controls the type of illumination 116 (e.g., UV light for fluorescent probes) and a selected set of fluorescent filters 114 which are used by digital imaging system 110 to acquire images of the specific probes. Once the images are acquired by digital imaging system 110 and the data is transferred to unit 122, unit 122 can identifies chromosomal aberrations, for example, by measuring the relative intensity of one stain (having at least two occurrences in the sample) in the selected ROIs, and comparing such relative intensity to a pre-defined amount index.

It will be appreciated that the methods of analyzing stained biological samples, identifying chromosomal aberrations, identifying genetically abnormal cells and/or the methods of scanning the sample using randomly or randomized scanning can be stored on a computer readable storage medium such as a magnetic, optico-magnetic or optical disk to thereby include the instructions for executing the methods of the present invention, as well as for storage of the amount indexes which can be used with each stain.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N. Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

User-Defined Ratio Between Spot Intensities Enables Accurate Analysis of Merged Spots FISH analysis may often result in merged signals (i.e., two spots which form one big spot) which can be subjected to false interpretation by the currently available automatic image analysis methods. An example is provided in FIG. 1. FIG. 1 shows a region of interest (ROI) of a FISH experiment using probes derived from the centromere of chromosome 10 (Red) and the centromere of chromosome 4 (Green). DAPI was used as a counterstaining (blue) to allocate the area of the nuclei. In a normal cell the two FISH probes result in two red and two green spots (see for example, cell No. 5 of FIG. 1). In an abnormal cell such as cell No. 7 of FIG. 1, there are three copies of chromosome 4 and three copies of chromosome 10. However, in some cells the observed FISH signals are more complicated. For example, as is shown in cell No. 1 of FIG. 1, the two red spots representing two copies of chromosome 10 are merged and form one big spot which can be mistakenly considered as monozomy for chromosome 10. It will be appreciated that using common image analysis software, such as those available from Applied Imaging, Olympus or Zeiss, analysis of cell No. 1 of FIG. 1, which is based solely on counting the number of spots, will result in wrong interpretation of the FISH signals (e.g., monozomy 10).

While reducing the present invention to practice, the present inventors uncovered that an image analysis software can measure the intensity of the spot and compare such intensity to the intensity of another spot present in the same or other cell(s) or to an average spot intensity as calculated based on measuring intensities of all the spots in a selected image(s) or specimen, thus enabling a correct diagnosis using computer-controlled analysis. Briefly, following image capture, the image analysis software measures the intensity of all the spots that belong to the same probe (e.g., the integrated intensity from all the pixels having an intensity higher than a certain threshold). Once measured, the intensity of a specific spot (i.e., the spot which is currently analyzed) is compared to the intensity of other spots, or to the average intensity of all spots from a single nucleus (or cell), or to the average intensity of spots that belong to that probe from more than one nucleus, and/or to the intensity of a reference spot previously defined by the user. Next, the ratio between such intensities is calculated and compared to a pre-defined ratio (e.g., defined by the user, preferably based on the specific probe used), thereby determining if the spot has the expected intensity ratio and can be further considered as a single spot or whether its intensity is bigger (or smaller as is further described in Example 2, hereinbelow) than expected (e.g., double, three times or more) and therefore can be considered as two spots which merged and formed one signal or as a partial or split spot as is further described in Example 2.

For example, in the case of spot No. I shown in cell No. 1 of FIG. 1, the intensity of the merged spot is twice of that of each of the spots marked in cell No. 6 of FIG. 1 (spots Nos. II and III) which can be defined as "reference spots" by the user. It will be appreciated that the average intensity of the red spots in the whole image or specimen can be similar to any of spots Nos. II or III. Once the image analysis software calculates the ratio between the intensity of the analyzed spot (e.g., spot No. I in cell No. 1 of FIG. 1) to an average spot intensity or to spot No. II or III in cell No. 6 of FIG. 1 (e.g., reference spot) such a ratio can be compared to a predetermined reference ratio such as "1" in a case of a normal cell and reveals that the ratio is bigger than expected (e.g., by a factor of two in this case). In this case the image analysis system of the present invention will notify the user that the spot has an intensity which is twice as much expected and/or can artificially split the two overlapping spots into two defined spots which can be therefore automatically counted.

Thus, this example demonstrates the advantage of measuring relative intensities of spots present in the image and comparing them to expected predetermined ratios for accurately analyzing stained specimens having merged signals.

Example 2

User-Defined Ratio Between Spot Intensities Enables Accurate Analysis of Translocations and/or Sub-Deletions The detection of translocations and sub-deletions can be performed using various kits employing probes that span the breakpoint region thus resulting in split signals. For example, the BCR/ABL translocation of chromosomes 9:22 can be detected by the split-signal kit available from DakoCytomation (Glostrup, Denmark) and as described in van Zutven LJCM et al., 2004, Two dual-color split signal fluorescence in situ hybridization assays to detect t(5; 14) involving HOX11L2 or CSX in T-cell acute lymphoblastic leukemia, Hematologica 89 p. 671-678. Another example is the TEL/AML1 (also known as ETV6/RUNX1) rearrangement, which is frequently found in childhood B-acute lymphoblastic leukemia (b-ALL). This fusion gene is caused by translocation of the TEL gene on chromosome 12p13 to the AML1 gene on chromosome 21q22 (Golub, T. R., et al., Proc. Natl. Acad. Sci. U.S.A. 92: 4917-4921, 1995). Detection of the TEL/AML1 fusion gene can be performed by the TEL/AML1 ES Dual Color Translocation Probe available from Vysis. This probe is a mixture of the LSI TEL probe (which begins between exons 3-5 and extends approximately 350 kb towards the telomere on chromosome 12) labeled with SpectrumGreen™ and the AML1 probe (an approximately 500 kb AML1 probe spans the entire gene) labeled with SpectrumOrange™. However, such analyses may often result in faint spots which can be mis-analyzed using the currently available image analysis techniques which are based on counting the spots, regardless of the relative spot intensity.

On the other hand, by applying the additional step devised by the present inventors in which a ratio between the intensity of the analyzed spot and the intensity of another spot such as a reference spot (defined by the user) and/or to an average intensity of several spots (e.g., which are measured from one or more cells or nuclei) is calculated and compared to a reference ratio, a correct interpretation of the FISH signals can be achieved. According to the method of the present invention, the system captures the information on stained biological samples and classifies a population of cells based on the relative intensity of at least one of the stained spots that are found in each cell.

As in prior art methods, the intensity of a spot is calculated by measuring the intensity of all pixels comprised in the spot (above a certain threshold). However, in sharp contrast to prior art methods, such an intensity of a spot is compared to the intensity of another spot (e.g., the average spot intensity) and the ratio therebetween is calculated and further compared to a pre-defined ratio or a reference ratio. According to the method of the present invention a deviation from an expected ratio or, on the other hand, the presence of a certain ratio is indicative of a chromosomal abnormality.

For example, the system (with the image analysis software) can measure the intensity of all spots present in the image and classify the spots according to their intensities. For example, spots Nos. II (of cell 1, FIG. 2) and V (of cell 2, FIG. 2) exhibit similar intensities and therefore can be classified in a single group (e.g., with an intensity of 10 arbitrary units). On the other hand, spots Nos. III (of cell 1, FIG. 2) and VI (of cell 2, FIG. 2), which exhibit similar and reduced intensity (e.g., with an intensity of 2-4 arbitrary units) as compared to the average intensity of spots Nos. II and V, can be classified in a separate group. Next, the system can use an additional stain such as the blue nuclear counterstaining (e.g., DAPI in this case) to allocate the stained spots to single cells (e.g., spots Nos. I-IV to cell 1 and spots Nos. V-VIII to cell 2, FIG. 2). Once allocated to cells (or nuclei) the intensity of each spot is compared to an average intensity of one class of spots and the ratio therebetween is calculated. The user can pre-define in the system (i.e., "teach the system") that the presence of two spots in the same cell with a specific ratio of spot intensities obtained with a certain probe is indicative of a certain chromosomal abnormality. For example, in case of using the TEL/AML1 ES Dual Color the presence of a ratio of about 0.2-0.4 between the analyzed spot to another spot present (allocated) in the same nucleus can indicate the presence of a translocation resulting in the TEL/AML1 fusion gene. Such a ratio can be seen between the intensities of spots Nos. III and II in cell 1 (FIG. 2) and/or between the intensities of spots Nos. VI and V in cell 2 (FIG. 2).

Alternatively, the calculated intensity ratio between the analyzed spot and another spot (e.g., an average spot intensity) can be compared to a reference ratio and if the calculated intensity ratio is significantly different from that of a reference ratio, the system notifies the user of such a deviation from the expected intensity ratio which can be interpreted accordingly as a spilt signal suggesting the presence of a genetic aberration such as a presence of a deletion, translocation, alternative splicing (e.g., split exons) and the like.

Another example of using the method and system of the present invention is provided in FIGS. 3*a-b*. FISH analysis was performed on bone marrow samples using the TEL/AML1 ES Dual Color Translocation Probe and the user pre-defined that an intensity ratio of about 0.2-0.4 between two spots of the same fluorescence (e.g., the SpectrumOrange™) in the same cell is indicative of the TEL/AML1 fusion gene. As is shown in FIG. 3*a*, the intensity ratio between spot No. VI and V of cell 1, spot No. I and II of cell 2, or spot Nos. VIII and VII of cell 3 is about 0.3, indicative of the presence of the TEL/AML1 fusion gene (i.e., translocation) in bone marrow cells of that sample. On the other in another bone marrow sample that is shown in FIG. 3*b*, the intensity ratio between spots Nos. III and IV of cell 1 or spots Nos. VIII and IX of cell 3 of is about 1, therefore indicating the absence of the TEL/AML1 fusion gene in these cells. In addition, it is noteworthy that the intensity of spot No. VII of cell 2 (FIG. 3*b*) can be analyzed as a merged signal (according to the teachings described in Example 1, hereinabove) and can be therefore split to two artificial spots.

Thus, detection of spilt spots (e.g., as a result of a chromosomal aberration such as a translocation or sub-deletion) can be done automatically using an image analysis software in which the user defines as an input a split signal (in terms of relative ratios) and the image analysis software uses that information and produces an output which includes the presence or absence of the genetic aberration (e.g., a translocation and/or a sub-deletion) and the degree (i.e., percentages) of genetic material which is missing or that was transferred to another chromosome as compared to a non-deleted, non-translocated chromosome. In addition, the system can calculate the frequency of genetically abnormal cells (e.g., cells having a chromosomal aberration) from the total cells in the sample (e.g., percentage of cancerous cells).

Such a step improves the analysis and the precision of the classification due to all the problems mentioned hereinabove. This method improves prior methods that only relate to the number of spots labeled with each probe, but in which the intensity ratio is not taken into account. The invention is important especially in cases where automation is required, so that the whole process becomes more accurate, and the improved algorithm provides an internal control on the data that is provided to the user.

Example 3

Automatic Selection of Region of Interest

When scanning a slide automatically, the area that is being scanned on the slide is usually much larger than the region-of-interest (ROI) that can be captured by the imaging system (due to the magnification of the optics). As an example, if the relevant area on the slide is 1 cm×1 cm, and the area of the CCD camera is 5 mm×5 mm (such area is in a typical range), and if a magnification of 20× is used in the microscope, it means that 1600 images have to be captured in order to cover the whole slide. This can take a long time, especially in fluorescence imaging where the signal is not so bright and exposure times in the range of seconds have to be used. For example, assuming an exposure time of 1 second is used, and the image have to be acquired through 2 different filters, and there is another 1 second extra time per frame for focusing and motion purposes, it will take 80 minutes to scan the slide. In many cases the time can be significantly reduced. As an example, in some cases it is enough to measure only a certain number of cells from the slides, say 300, so that the scanning can stop after achieving this number.

A simple way of doing that is to start scanning at the center of the slide and start scanning in a circular manner image after image outward. This method performs well if the population of cells is evenly distributed on the slide, a condition that is usually not fulfilled. It will therefore lead to two problems:
1. In some cases, the scanning will start in an area that is completely irrelevant, either because of biological reasons, or because it happened to be an area that has no cells due to non-uniform sample preparation, and therefore a lot of time is wasted until a relevant area is reached.
2. It may happen that the population of cells that is measured at the center of the slide (or in any other area) belongs mainly to one biological class while other classes are distributed in other areas. This may be very relevant especially in the case of tissues of cells, where there may be only a small section of a tumor (as an example), and this part may be completely skipped during the scan suggested above.

In order to overcome these problems and significantly allow for a shorter scan time, that at the same time also ensures a much more reliable method that correctly sample the area of the slide, a new scanning strategy is provided. Such scanning strategy scans the slide in a random or randomized scanning mode.

The random scanning strategy—scans the relevant area on the slide by selecting random x and y coordinates selected according to a different statistical distribution, such as a uniform or a Gaussian distribution with appropriate parameters within the relevant range. The method can be further improved by excluding points that were already scanned from being scanned again. This method will ascertain a random coverage of the scanned region.

Randomized scanning: semi-random scanning strategy—is invented whereby the sample is scanned by using a random procedure but in a structured format. As an example, the relevant sample area can be divided to 4×4 sub-regions, the images are scanned by selecting one image at a time from one of the 16 regions, but the specific area to scan within each sub-region is selected randomly. This method presents an improvement of the random scanning strategy described above.

Randomized scanning: semi-random cognitive scanning strategy—This method is more efficient in covering the whole relevant area while uniformly scanning it. Briefly, one starts at two given points, and then searches by jumping to the point that is farthest away from all the previous points, and continues in the same manner. In such a way the whole slide is scanned with a uniform distribution so that for each given number of frames that are captured, they are uniformly distributed in the relevant region. It is therefore an improved method relative to the systematic scanning methods that are used today (e.g., U.S. Pat. No. 6,215,892 to Douglas et al.).

Example 4

A System which Uses a Monochrome Camera and a Color Camera for Capturing Ina Single Exposure Information Obtained Using Multiple Stains As is mentioned in the background section hereinabove, many biological applications rely on the use of multiple stains on a single biological specimen. Detection of multiple stains on a single specimen is currently limited by the type of camera attached to the imaging system (i.e., either a color camera or a monochrome camera).

To overcome such limitations, the system developed by the present inventors includes both a monochrome camera and a color camera, defined as a camera that can capture, using distinct exposures, the information on at least two, but preferably three or more color channels. The system further includes a computer that controls the two cameras and determines which camera is used for which stain or stains combination. The selection of the appropriate camera depends also on the specific sample being imaged. In some cases, the brightness of a certain stain may be too weak, and therefore, the computer can determine (based on a pre-defined criteria) which camera to use during the acquisition of images.

This system is of special importance when using scanning stations in which the speed is the most important parameter. Both scans can be done either by color camera or by monochrome camera, but in each such case speed will not be optimal for all stains.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of analyzing a labeled biological sample, the method comprising measuring a relative amount of at least one label having at least two occurrences in the labeled biological sample, thereby analyzing the labeled biological sample.

2. The method of claim 1, wherein the sample comprises a DNA sample or an RNA sample.

3. A method of identifying a chromosomal aberration comprising:
   (a) in situ staining a chromosome being comprised in a cell of a sample with a nucleic acid probe having at least one label; and
   (b) microscopically analyzing a relative amount and optionally a frequency of said at least one label of said nucleic acid probe in said cell, said at least one label having at least two occurrences in said sample, wherein said relative amount and optionally said frequency of said at least one label in said sample are indicative of the chromosomal aberration, thereby identifying the chromosomal aberration.

4. The method of claim 3, wherein measuring said relative amount comprises computationally scanning said sample.

5. The method of claim 4, wherein said scanning comprises randomized scanning of said sample.

6. The method of claim 5, wherein said randomized scanning comprises randomly scanning an area of at least a portion of a plurality of selected sub-regions of said sample.

7. The method of claim 4, wherein said computationally scanning is effected by a computer-controlled imaging system.

8. The method of claim 7, wherein said computer-controlled imaging system comprises an optical microscope, a digital imaging system and a computer.

9. The method of claim 8, wherein said digital imaging system comprises at least one camera selected from the group consisting of a monochrome camera and a color camera.

10. The method of claim 8, wherein said digital imaging system comprises a monochrome camera and a color camera.

11. The method of claim 9, wherein said monochrome camera comprises a black and white array detector.

12. The method of claim 9, wherein said color camera allows measuring of at least two color channels.

13. The method of claim 9, wherein said color camera allows measuring of at least three color channels.

14. The method of claim 3, wherein said at least two occurrences are comprised in a single cell.

15. The method of claim 3, wherein said at least two occurrence are comprised in different cells.

16. The method of claim 3, further comprising correlating said relative amount to an amount index following said measuring of said relative amount.

17. The method of claim 3, further comprising correlating said frequency of said at least one label to a frequency index following said measuring said frequency of at least one label.

18. The method of claim 3, wherein said at least one nucleic acid probe is a fluorescence in situ hybridization (FISH) probe.

19. The method of claim 3, further comprising identifying the cell nucleus of the cell.

20. A method of identifying a genetically abnormal cell in a sample, the method comprising:
   (a) in situ staining a chromosome being comprised in a cell of said sample with a nucleic acid probe having at least one label; and
   (b) microscopically analyzing a relative amount and optionally a frequency of said at least one label of said nucleic acid probe in said cell, said at least one label having at least two occurrences in the sample, wherein said relative amount and optionally said frequency of said at least one label in the cell are indicative of a chromosomal aberration, thereby identifying the genetically abnormal cell in the sample.

21. The method of claim 20, further comprising identifying the cell nucleus of the cell.

* * * * *